United States Patent
Jerussi et al.

(12) 
(10) Patent No.: US 6,303,145 B2
(45) Date of Patent: *Oct. 16, 2001

(54) (S,R) FORMOTEROL METHODS AND COMPOSITIONS

(75) Inventors: Thomas P. Jerussi, Framingham; Chris Hugh Senanayake, Shrewsbury, both of MA (US)

(73) Assignee: Sepracor Inc., Marlborough, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/309,154

(22) Filed: May 10, 1999

(51) Int. Cl.$^7$ ............... A61K 9/20; A61L 9/04; A01N 37/00; A01N 33/02
(52) U.S. Cl. ............... 424/464; 424/45; 514/576; 514/553; 514/653; 514/826
(58) Field of Search ............... 424/464, 478, 424/45; 514/826, 653, 554, 960, 964, 553, 576, 630

(56) References Cited

U.S. PATENT DOCUMENTS

| | | | |
|---|---|---|---|
| 4,814,161 | 3/1989 | Jinks | 424/45 |
| 4,975,466 | 12/1990 | Böttcher et al. | 514/630 |
| 5,795,564 | 8/1998 | Aberg et al. | 424/45 |
| 6,040,344 | * 3/2000 | Gao et al. | 514/554 |

FOREIGN PATENT DOCUMENTS 2255503   11/1992   (GB).

WO92/05147   4/1992   (WO).

OTHER PUBLICATIONS

Hett, R. et al. "Large-Scale Synthesis of Enantio- and Diastereomerically Pure (R, R) –Formoterol..." *Org. Proc. Res. & Dev. 2*, 96–99 (1998).

Hett, R. et al. "Enantio- and Diastereoselective Synthesis of all Four Stereoisomers..." *Tet, Lett. 38*, 1125–1128 (1997).

Testa et al. "Racemates Versus Enantiomers in Drug Development: Dogmatism..." *Chirality 2*, 129–133 (1990).

Trofast et al. "Steric Aspects of Agonism and Antagonism at β–Adrenoceptors; Synthesis..." *Chirality 3*, 443–450 (1991).

Hett et al. "Conformational Toolbox of Oxazaborolidine Catalysts in the Enantioselective..." *Tet. Lett. 39*, 1705–1708 (1998).

Murase et al. "Absolute Configurations of Four Isomers of 3–Formamido–4–hydroxy–..." *Chem. Pharm. Bull. 26*, 1123–29 (1978).

Ariëns "Racemic therapeutics–ethical and regulatory aspects" *Eur. J. Clin. Pharmocol 41*, 89–93 (1991).

Ariëns "Stereoselectivity in pharacodynamics and pharmacokinetics" *Schweiz. med. Wochenschr. 120*, 131–134 (1990).

* cited by examiner

*Primary Examiner*—Michael G. Hartley
(74) *Attorney, Agent, or Firm*—Heslin Rothenberg Farley & Mesiti P.C.

(57) ABSTRACT

A method and composition are disclosed utilizing the pure (S,R) isomer of formoterol, which is a bronchodilator with reduced adverse effects. (S,R)-Formoterol may be conveniently and safely formulated for aerosol administration.

17 Claims, No Drawings

(S,R) FORMOTEROL METHODS AND COMPOSITIONS

FIELD OF THE INVENTION

The invention relates to pharmaceutical compositions and methods employing optically pure (S,R) formoterol.

BACKGROUND OF THE INVENTION

Asthma, bronchitis and emphysema are known as Chronic Obstructive Pulmonary Diseases (COPD). COPD is characterized as generalized airways obstruction, particularly of small airways, associated with varying degrees of symptoms of chronic bronchitis, asthma, and emphysema. The term COPD was introduced because these conditions often coexist, and it may be difficult in an individual case to decide which is the major condition producing the obstruction. Airways obstruction is defined as an increased resistance to airflow during forced expiration. It may result from narrowing or obliteration of airways secondary to intrinsic airways disease, from excessive collapse of airways during a forced expiration secondary to pulmonary emphysema, from bronchospasm as in asthma, or may be due to a combination of these factors. Although obstruction of large airways may occur in all these disorders, particularly in asthma, patients with severe COPD characteristically have major abnormalities in their small airways, namely those less than 2 mm internal diameter, and much of their airways obstruction is situated in this zone. The airways obstruction is irreversible except for that which can be ascribed to asthma.

Asthma is a reversible obstructive pulmonary disorder (ROPD) characterized by increased responsiveness of the airways. Asthma can occur secondarily to a variety of stimuli. The underlying mechanisms are unknown, but inherited or acquired imbalance of adrenergic and cholinergic control of airways diameter has been implicated. Persons manifesting such imbalance have hyperactive bronchi and, even without symptoms, bronchoconstriction may be present. Overt asthma attacks may occur when such persons-are subjected to various stresses. Persons whose asthma is precipitated by allergens (most commonly airborne pollens and molds, house dust, animal danders) and whose symptoms are IgE-mediated are said to have allergic or "extrinsic" asthma. They account for about 10 to 20% of adult asthmatics; in another 30 to 50%, symptomatic episodes seem to be triggered by non-allergenic factors (e.g., infection, irritants, emotional factors), and these patients are said to have nonallergic or "intrinsic" asthma.

Formoterol (1), whose chemical name is (+/−) N-[2-hydroxy-5-[1-hydroxy-2[[2-(p-methoxyphenyl)-2-propyl]amino]ethyl]phenyl]-formamide is a highly potent and $\beta_2$-selective adrenoceptor agonist having a long lasting bronchodilating effect when inhaled. The structure of formoterol is as shown:

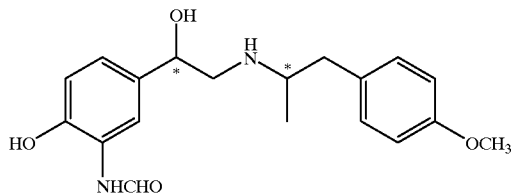

Formoterol's primary use is as a long-acting bronchodilator for the relief of reversible bronchospasm in patients with obstructive airway disease such as asthma, bronchitis and emphysema.

The class of $\beta_2$ agonists, of which formoterol is a member, cause somewhat similar adverse effects. These adverse effects include but are not limited to central nervous system symptoms, such as hand tremors, muscle tremors, nervousness, dizziness, headache and drowsiness; respiratory side effects, such as dyspnea, wheezing, drying or irritation of the oropharynx, coughing, chest pain and chest discomfort; and cardiovascular effects, such as palpitations, increased heart rate, and tachycardia. According to Trofast et al. (op. cit.) (R,R) formoterol is primarily a chronotropic agent in vitro with inotropic effects showing up at higher concentrations. The chronotropic effects are reported at concentrations that are higher than those at which relaxation of tracheal muscle (bronchodilation) is seen. β-Agonists (e.g. dobutamine) are known in general to exhibit inotropic activity. In addition, racemic $\beta_2$-agonists can cause angina, vertigo, central stimulation and insomnia, airway hyperreactivity (hypersensitivity), nausea, diarrhea, dry mouth and vomiting. As with other pharmaceuticals $\beta_2$-agonists sometimes cause systemic adverse effects such as weakness, fatigue, flushed feeling, sweating, unusual taste, hoarseness, muscle cramps and backaches.

Furthermore, patients may develop a tolerance to the bronchodilating effect of the racemic mixture of formoterol. This is related to desensitization, which is one of the most clinically significant phenomena involving the beta-adrenergic receptor. The problem of desensitization is especially significant in the treatment of diseases involving bronchospasms, such as asthma. The treatment of asthma usually involves the self-administration, either orally or by aerosol, of beta-adrenergic agonists such as the racemic (R,R) (S,S) mixture of formoterol. These agonists mediate bronchodilation and promote easier breathing. Asthmatic patients utilizing β-agonists for a prolonged time gradually increase the self-administered dose in order to get a sufficient amount of bronchodilation and relief in breathing. As a result of this increased dosage, the agonist concentration builds to a sufficient level so as to enter the peripheral circulation where it acts on the beta receptors of the heart and vasculature to cause cardiovascular stress and other adverse effects.

Formoterol has two chiral centers (denoted by the asterisks in formula 1), each of which can exist in two possible configurations. This gives rise to four combinations: (R,R), (S,S), (R,S) and (S,R). (R,R) and (S,S) are mirror images of each other and are therefore enantiomers; (R,S) and (S,R) are similarly an enantiomeric pair. The mirror images of (R,R) and (S,S) are not, however, superimposable on (R,S) and (S,R), which are diastereomers. Formoterol is available commercially only as a mixture of (R,R) plus (S,S) in a 1:1 ratio, and the generic name formoterol refers to this racemic mixture. The racemic mixture that is commercially available for administration is a dihydrate of the fumarate salt of the formula shown:

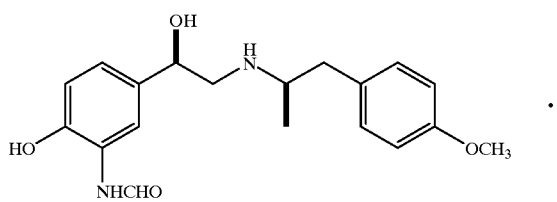

-continued

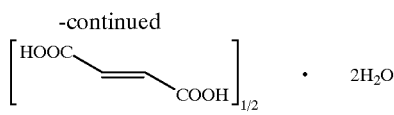

The graphic representations of racemic, ambiscalemic and scalemic or enantiomerically pure compounds used herein are taken from Maehr *J. Chem. Ed.* 62, 114–120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, the formula for formoterol above reflects the racemic nature of the commercial material, while among the structures below, those having open wedges are intended to encompass a pure, single configuration which is one of the two possible at that carbon, and those having solid wedges are intended to encompass the single, pure isomer having the absolute stereochemistry shown.

3-Amino-4-hydroxy-α-[[[2-(4-methoxyphenyl)-1-methylethyl]amino]methyl]-benzenemethanol (Chem. Abst. Reg. No. 150513-24-9). which is referred to hereinafter as "desformoterol" (2), has been disclosed as an undesired side product in a synthesis of formoterol (Spanish Patent ES 2031407). Its structure is shown below.

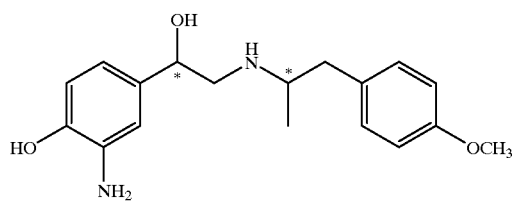

Neither its deliberate synthesis nor its pharmacology has been previously reported. It too exists in four isomeric forms.

All four isomers of formoterol have been synthesized and briefly examined for relaxing activity on the guinea pig trachea [Murase et al., *Chem. Pharm. Bull.* 26, 1123–1129 (1978). It was found that the (R,R)-isomer is the most potent, while the others are 3–14 times less potent. More recently, the four isomers have been examined with respect to their ability to interact in vitro with β-adrenoceptors in tissues isolated from guinea pig [Trofast et al., *Chirality* 3, 443–450 (1991)]. The order of potency was (R,R)>>(R,S)=(S,R)>(S,S). It was found that the (R,R)-isomer is 1000-fold more potent than the (S,S)-isomer. Trofast concluded that "Since the (S,S)-enantiomer is practically inactive there is from this point of view no reason for its removal from the racemate in pharmaceutical preparations . . . " In contradistinction, U.S. Pat. No. 5,795,564 indicates that administration of the pure (R,R)-isomer provides significant therapeutic advantages, particularly in avoiding or ameliorating the side effects seen with racemic formoterol (i.e. 1:1 RR/SS isomers). No art appears to suggest any advantage to the use of the pure S,R isomer. In fact, it is one of the two isomers that has for twenty years been removed from the commercial formoterol product.

Thus the general conclusion among persons of skill in the art is that, if there is any advantage to an individual isomer, it resides in the R,R isomer. However, we have discovered that there are practical problems associated with the preparation of pharmaceutical dosage forms of racemic and R,R formoterol. These problems arise from the extraordinary potency of racemic and R,R formoterol; it is simply too potent to conveniently formulate for a metered dose inhaler. Since it is active on. the microgram level, if even a small amount of active ingredient sticks to the inhaler, e.g. to the valve components or other interior portions of the canister, significant overdosing can arise when it is released on a subsequent activation. There is therefore a need for a medicament having the advantages of R,R formoterol but less potential for dose-to-dose variability in formulations.

SUMMARY OF THE INVENTION

The present invention relates to compositions and methods employing the S,R isomer of Formoterol (3). These compositions may also include S,R-desformoterol (4), which has a similar pharmacological profile:

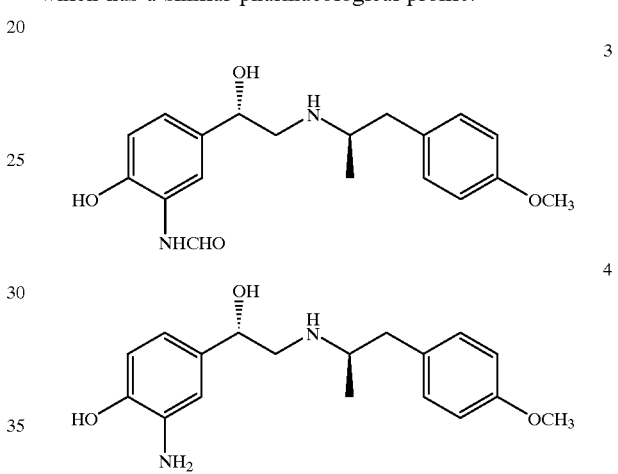

It has now been discovered that the (S,R) isomer of formoterol is an effective bronchodilator that may be safely formulated for reproducible aerosol administration. It possesses similar $\beta_2$ selectivity to that of the corresponding R,R isomer and therefore avoids certain adverse effects associated with the racemic form.

In one aspect the invention relates to methods of inducing bronchodilation or preventing bronchoconstriction with (S,R) formoterol comprising administering to an individual a therapeutically effective amount of (S,R)-formoterol, which is a quantity of (S,R) formoterol sufficient to induce bronchodilation or prevent bronchoconstriction. The (S,R) formoterol may be administered orally or by subcutaneous injection, intravenous infusion, inhalation, or transdermal delivery. Inhalation is preferred. Preferably the (S,R)-formoterol contains less than 10% by weight of other isomers of formoterol, and in particular, less than 1% by weight of the R,R enantiomer. More preferably the (S,R)-formoterol contains less than 5% by weight of other isomers of formoterol; most preferably the (S,R)-formoterol contains less than 2% by weight of other isomers of formoterol. The amount administered by inhalation is about 100 µg to about 10 mg per day, in single or divided doses.

The present invention also includes pharmaceutical compositions containing (S,R) formoterol of the optical purity described above. The pharmaceutical compositions may be in the form of a tablet, capsule or aerosol formulation, and they comprise a pharmaceutically acceptable carrier suitable for a tablet, capsule or aerosol and an amount of (S,R)- formoterol, or a pharmaceutically acceptable salt thereof, sufficient to alleviate bronchospasms. Compositions for administration by inhalation contain about 600 μg to about 2.5 mg of (S,R) formoterol and the pharmaceutically acceptable carrier may include a propellant. Compositions for oral administration include syrups, tablets and capsules. Anhydrous compositions are preferred.

DETAILED DESCRIPTION OF THE INVENTION

The present invention encompasses a method of eliciting a bronchodilator effect while avoiding the concomitant liability of adverse effects or development of tolerance, which comprises administering to a human in need of bronchodilation an amount of (S,R) formoterol or (S,R) desformoterol sufficient to alleviate bronchospasms, but insufficient to cause said adverse effects, development of tolerance or hypersensitivity.

The present invention provides a method or use for the treatment of ROPD, in particular for effecting bronchodilatation, as a means of alleviating airways obstruction, in particular acute airways obstruction, e.g. asthma attack, occurring in such disease. The invention thus provides symptomatic therapy for such disease. The present invention is applicable in the therapy of obstructive airways disease and, in general, any such disease for which $\beta_2$ agonists are commonly employed in therapy.

The present invention provides means to avoid, ameliorate or restrict deleterious side effects observed in patients consequent to conventional clinical usage of $\beta_2$ agonists as racemic mixtures, for example "anomalous", "rebound" or "paradoxical" bronchospasm and, especially, increase in airway obstruction, exacerbation of late asthmatic response or non-specific bronchial reactivity or arterial hypoxemia.

A mixture of formoterol isomers can be prepared according to U.S. Pat. No. 3,994,974. The diastereomers may be separated as described by Murase et al. [*Chem. Pharm. Bull.* 25, 1368–13 (1977)]. The individual isomers of formoterol may be obtained as described by Trofast et al. (op. cit.) by stereocontrolled synthesis from optically active starting material or by resolution of a mixture of enantiomers (i.e., the racemic mixture) using conventional means, such as an optically active resolving acid.

An enantioselective synthesis is described below:

To 800 mL of methanol were added 328 g of 4-methoxyphenylacetone (2 mol) and 214 g of N-benzylamine (2 mol). The imine formation was exothermic and the solution warmed to 45° C. After reaction was complete. the solution was hydrogenated at 50 psi for 6–8 hours in the presence of 3.3 g of 5% platinum on carbon catalyst. When the hydrogen uptake had stopped, the reaction was filtered through diatomaceous earth, and the filter cake was washed with 200 mL of methanol. The combined filtrates were placed in a 6-liter flask and diluted with 4.2 liters of methanol. (S)-L-Mandelic acid (304 g, 2 mol) was added and the mixture heated with stirring to reflux to obtain a clear solution. The solution was cooled to room temperature, stirred at room temperature for two hours and the mandelic acid salt filtered off. The recrystallization was repeated three times to obtain 60–70 g of 4-methoxy-α-methyl-N-(phenylmethyl)benzeneethaneamine L-mandelic acid salt having an isomeric purity greater than 99.8% and a melting point of 164° C.

A 5-liter flask was charged with 300 g (1.1 mol) of 4-benzyloxy-3-nitroacetophenone and 3 liters of acetonitrile. The mixture was heated to 50° C. to form a clear solution, and 180 g of bromine (1.6 mol) was added in one portion. The reaction was stirred at 50° for 15–25 minutes, during which time the deep red color changed to pale orange and TLC (ethyl acetate/hexane 3:7) showed no remaining starting material. Without heating, 200 to 300 mL of acetonitrile, along with the byproduct hydrogen bromide, were distilled from the reaction under vacuum. During the course of the distillation, the temperature dropped to about 15° and the product precipitated as a yellow solid. The reaction was stirred at 0–5° for two hours and the product filtered off and washed with acetonitrile. The resulting 2-bromo 4'-benzyloxy-3' nitroacetophenone was dried in vacuum to yield 242 g (63%) of off-white solid having a melting point of 136° C.

In an improved procedure, bromine was replaced by pyridinium tribromide and the bromination was carried out at room temperature. The 2-bromo-4'-benzyloxy-3'-nitroacetophenone product was isolated by addition of water.

A 2-liter flask is charged with 2.5 g (17 mmol) of (1S,2R)-aminoindanol in 50 mL of THF under argon. While cooling to maintain a temperature below 25° C., 3.4 mL (34 mmol) of a 10 mol solution of borane methyl sulfide is added over a period of 5 minutes and the reaction stirred for ten minutes at 25° C. to complete formation of the catalyst. To this catalyst solution the ketone and reducing agent are added simultaneously. From separate reservoirs are added (1) a solution of 120 g of 2-bromo-4'-benzyloxy-3'-nitroacetophenone (0.34 mol) in 950 mL of THF and (2) 24 mL of 10 M borane-methyl sulfide. Addition is over a period of 3 hours at 25° C. The reaction is cooled on an ice bath and 100 mL of methanol is added over a period of 15 minutes. The reaction mixture is concentrated under vacuum to a volume of about 200 mL, and 650 mL of toluene is added to dissolve the residue. The solution is washed with 0.2 M sulfuric acid and then water. If desired the aminoindanol may be recovered from the aqueous acidic phase. The organic phase was dried over sodium sulfate, filtered and concentrated to a weight of 240–260 g. A total of 100 mL of heptane is added to the mixture with stirring at 50–60°, then cooled to 15–20° and filtered. The wet filter cake may be used in the next step without drying or the solid may be dried under vacuum to give (S)-α-(bromomethyl)-4-phenylmethoxy-3-nitrobenzemethanol as an off white solid, melting point 68° C.

An alternative reduction employs borane-diethylaniline: A 50-liter flask is charged with 70 g (0.5 mol) of (1S,2R)-aminoindanol in 10 L of THF under argon. While cooling to maintain a temperature below 25° C., 1.9 L (10 mol) of a 5.6 M solution of borane diethylaniline is added over a period of 20 minutes and the reaction stirred for 30 minutes at 15–25° C. to complete formation of the catalyst. The solution is cooled to 0–5° C. and a carefully dried solution of 3.5 kg of 2-bromo-4'-benzyloxy-3'-nitroacetophenone (10 mol) in 32 L of THF is added over a period of at least 2 hours at 0–5° C. After addition is complete, 3.9 L of acetone is added over a period of 20 minutes, keeping the temperature at 5–15° C. The reaction mixture is concentrated under vacuum to a volume of about 10.5 L, and 24 L of toluene is added to dissolve the residue. The solution is washed with 1.0 M sulfuric acid and then brine. The organic phase is concentrated to a volume of 10.5 L twice with toluene to reduce the water to <0.02% by Karl Fischer titration. The mixture is cooled with stirring to 24° C. and seeded, then cooled very slowly to 20° and 7.2 L of heptane is added to the slurry with stirring. The mix is filtered and rinsed with heptane. The solid is dried at 25° C. to give (S)-α-(bromomethyl)-4-phenylmethoxy-3-nitrobenzemethanol.

A solution of 100 g (0.28 mol) of (S)-α-(bromomethyl)-4-phenylmethoxy-3-nitrobenzemethanol in 200 mL of THF and 200 nL of toluene is hydrogenated in a Parr hydrogenator in the presence of 1 g of platinum oxide catalyst at 45–50 psi for 7–13 hours until hydrogen uptake ceases. The reaction mixture is filtered through a bed of diatomaceous earth and a solution of 21.5 g (0.48 mol) of formic acid and 33 g (0.32 mol) of acetic anhydride, which have been pre-mixed, is added to the filtrate, which is maintained at 10–15° C. by external cooling. The solution is stirred for 20 minutes at 10–25° C. and then concentrated to about 300 mL at 30° C. One hundred milliliters of toluene is added and the reaction is stirred at 15° C. for 15 minutes. The resulting slurry is filtered to provide (S)—N-[5-(2-bromo-1-hydroxyethyl)-2-(phenylmethoxy)phenyl]formamide having a melting point 130° C., isomeric purity 99–99.5%. The product is also sometimes referred to as 2-bromo-(4'-benzyloxy-3'-formamidophenyl)ethanol.

An alternative reduction using 6 g of 10% platinum on carbon and 0. 12–0.5 g of dimethyl sulfide, with no toluene, gives cleaner product when $BH_3$ THF is used as the reducing agent in the previous step. The use of 30 g of formic acid to prepare the mixed anhydride may improve yields.

A 2-liter flask was charged with 75 g of (S)—N-[5-(2-bromo-1-hydroxyethyl)-2-(phenylmethoxy)phenyl]-formamide (0.21 mol), 92 g of (R)-4methoxy-α-methyl-N-(phenylmethyl)benzene-ethaneamine L-mandelic acid salt (0.23 mol), 75 g of milled potassium carbonate (0.6 mol, 325 mesh), 425 mL of THF and 425 mL of methanol. The mixture was stirred under argon at 25° until <0.5% of the formamide starting material remained. The mixture was concentrated to approximately 550 mL, by distillation. To the residue was added 225 mL of toluene and the mixture was distilled again to 500 mL. This was repeated twice and the final volume reduced to about 225 mL. Five hundred milliliters of water was added. The slurry was stirred 10 minutes, the phases were separated and the slurry and separation processes repeated. The toluene solution was disitiled under vacuum at 120° C. to completely remove the toluene. The residue was stirred at 120° C. until less than 2.5% of the N-benzyl-2-amino-(4-methoxyphenyl)propane remained (about 8 hours). The solution was cooled to 83° C. and 100 mL of carbon tetrachloride was added. The carbon tetrachloride solution was poured onto a silica gel column and flash chromatographed with cyclohexane/dichloromethane/MTBE (2:1:1) to yield 24 g of dibenzyl protected formnoterol.

The S,R dibenzyl protected formnoterol (13.84 g) was dissolved in 28 mL of ethanol and transferred to a Parr hydrogenator and hydrogenated at 45–50 psi in the presence of 1.9 g of 10% palladium on carbon until hydrogen uptake was complete (3–4 hours) and less than 0.5% of the monobenzyl formoterol remained. The mixture was filtered through a pad of diatomaceous earth and washed with 25 mL of ethanol. The ethanol was removed in vacuo and 78 mL of 2-propeanol was added. The mixture was heated to reflux until a clear solution was formed. As soon as the clear solution formed, heating was discontinued and the mixture was cooled to 23°, at which temperature it was held for 2 days. The product was collected by filtration, washed with 2-propanol and dried under vacuum to provide 3.69 g of (S,R) formoterol free base.

The magnitude of a prophylactic or therapeutic dose of (S,R) formoterol in the acute or chronic management of disease will vary with the severity of the condition to be treated, and the route of administration. The dose, and perhaps the dose frequency, will also vary according to the age, body weight, and response of the individual patient. In general, the total daily dose ranges when administered by inhalation, for the conditions described herein, is from about 100 $\mu$g to about 10 mg, in single or divided doses. Preferably, a daily dose range should be between about 600 $\mu$g to about 2.5 mg, in single or divided doses, while most preferably, a daily dose range should be between about 1.2 mg to about 2.5 mg, in from two to four divided doses. In managing the patient, the therapy should be initiated at a lower dose, perhaps about 300 $\mu$g to about 1.2 mg, and increased up to about 2×1.2 mg or higher depending on the patient's global response. When administered orally, preferably as a tablet, the preferred dose range is from 10 to 100 mg per day. It is further recommended that children, and patients over 65 years, and those with impaired renal, or hepatic function, initially receive low doses, and that they be titrated based on individual responses) and blood level(s). It may be necessary to use dosages outside these ranges in some cases as will be apparent to those skilled in the art. Further, it is noted that the clinician or treating physician would know how and when to interrupt, adjust, or terminate therapy in conjunction with individual patient response.

The terms "an amount sufficient to alleviate bronchospasms but insufficient to cause said adverse effects" are encompassed by the above-described dosage amounts and dose frequency schedule.

Any suitable route of administration may be employed for providing the patient with an effective dosage of (S,R) formoterol. For example, oral, rectal, parenteral (subcutaneous, intramuscular, intravenous), aerosol, transdermal, and like forms of administration may be employed. Dosage forms include tablets, troches, dispersions, suspensions, solutions, capsules, patches, and the like.

The pharmaceutical compositions of the present invention comprise (S,R) formoterol and/or (S,R) desformoterol as the active ingredient, or a pharmaceutically acceptable salt thereof, and may also contain a pharmaceutically acceptable carrier, and optionally, other therapeutic ingredients. The term "pharmaceutically acceptable salts" or "a pharmaceutically acceptable salt thereof" refer to salts prepared from pharmaceutically acceptable nontoxic acids including inorganic acids and organic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, and the like. The fumaric and tartaric acid salts are particularly preferred.

The compositions of the present invention include compositions such as suspensions, solutions, elixirs; aerosols and solid dosage forms, with carriers such as starches, sugars, microcrystalline cellulose, diluents, granulating agents, lubricants, binders, disintegrating agents, and the like. The compositions include compositions suitable for oral, rectal, parenteral (including subcutaneous, transdermal, intramuscular, and intravenous) and inhalation, although the most suitable route in any given case will depend on the condition being treated and the nature and severity of that condition. The most preferred routes of the present invention are: (1) oral by either tablets or capsules, (2) inhalation and (3) transdermal by patch. They may be conveniently presented in unit dosage form and prepared by any of the methods well-known in the art of pharmacy.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; and 4,008,719, the disclosures of which are hereby incorporated by reference. Because they reduce peak plasma concentrations, controlled release dosage forms are particularly useful for oral administration in that they provide a therapeutic plasma concentration of S,R-desformoterol or S,R-formoterol while avoiding the side effects associated with peak plasma concentrations.

EXAMPLE 1

Formula for Inhalation

| Formula | Quantity contained in Each Metered Dose Dispenser |
|---|---|
| (S,R,)-formoterol | 180 mg |
| trichloromonofluoromethane | 15.16 g |
| dichlorodifluoromethane | 15.16 g |
| sorbitan trioleate | 1.05 g |

The metered dose dispenser contains micronized (S,R)-formoterol in suspension. Each actuation delivers 0.6 mg of (S,R)-formoterol from the mouthpiece. Each canister provides about 300 inhalations.

EXAMPLE 2

Compressed tablets

| | Per tablet | Per 10,000 tablets |
|---|---|---|
| (S,R)-Formoterol | 10 mg | 100 g |
| Starch | 60 mg | 600 g |
| Talc | 12 mg | 120 g |
| Acacia | 12 mg | 120 g |
| Stearic Acid | 1 mg | 10 g |

Tablets may be prepared using conventional wet granulation techniques, such that each dosage unit contains 0.1 mg to 10 mg of formoterol. The acacia and an equal weight of starch is blended to form a paste which is used to granulate the formoterol. The mixture is dried and placed through a mesh screen. The remainder of the material is added and mixed thoroughly. The resulting mixture is compressed into tablets using a 9/32-inch (7 mm) punch.

Sustained release tablets may be prepared by methods well known in the pharmaceutical art. (See Remington: The Science and Practice of Pharmacy 19th Edition 1995, Chapter 94 and U.S. Pat. No. 5,674,895 the disclosures of which are incorporated herein by reference.) An exemplary sustained release formulation is shown below.

EXAMPLE 3

Sustained release tablets

| | Per tablet | Per 10,000 tablets |
|---|---|---|
| (S,R)-Formoterol | 10 mg | 100 g |
| HPMC 2208 USP | 100 mg | 1000 g |
| Carnauba wax | 20 mg | 200 g |
| HPMC 2910 USP | 10 mg | 100 g |
| Talc | 5 mg | 50 g |
| Magnesium stearate | 1 mg | 10 g |
| Stearic Acid | 4 mg | 40 g |

The first three ingredients are placed in a granulator and mixed for 15 minutes. The hydroxypropylmethylcellulose is dissolved in water by warming and then cooled and sprayed onto the fluidized mixture. The granules are dried to 5% moisture. The last three ingredients are added sequentially with mixing. The mixture is compressed into tablets.

Another formulation that lends itself to aerosol administration of S,R-formoterol is a solid state open matrix network that allows one to quickly generate a precisely controlled volume of an aqueous solution suitable for aerosol administration. Preferably the solid state matrix disintegrates (dissolves or disperses) within 10 seconds or less. Such dosage forms are described in copending application Ser. No. 09/168,216, filed Oct. 7, 1998, the pertinent disclosure of which is incorporated herein by reference. The carrier material used may be any water-soluble or water-dispersible material that is pharmacologically acceptable or inert to the formoterol and that is capable of forming a rapidly disintegratable open matrix network. Use of a water-soluble material as the carrier results in the most rapid disintegration of the matrix when the product is placed in an aqueous medium. A particularly advantageous carrier may be formed from a protein such as gelatin, particularly partially hydrolyzed gelatin. The hydrolyzed gelatin is preferably used at concentrations of about 1 to 6% weight/volume based on the volume of the initial solution, prior to lyophilization. Other carrier materials include polysaccharides such as hydrolyzed dextran, dextrin and alginates (e.g. sodium alginate) or mixtures of above mentioned carriers with each other or with other carrier materials such as polyvinyl alcohol, polyvinylpyrrolidine or acacia. The solid state matrices may incorporate ingredients in addition to the medicament, for example coloring agents, flavoring agents, preservatives (e.g. bacteriostatic agents), and the like.

The solid state matrices are prepared by subliming (lyophilizing) solvent (usually water) from a composition comprising the formoterol and a solution of the carrier material in a solvent, the composition being in the solid state in a mold, which can be a reservoir for a nebulizer. Although the solvent is primarily water, it may contain a co-solvent such as t-butanol when necessary to improve the solubility of the medicament. The composition may also contain a surfactant e.g. Tween 90 [polyoxyethylene (20) sorbitan-mono-oleate] to aid in the dispersion of the medicament.

The mold may be in the form of a tray having a series of cylindrical or other shape depressions in it, each of a size corresponding to the desired size of the solid state matrix. Alternatively, the size of the depression may be larger than the desired size of the article and, after the contents have been freeze dried, the product can be cut into the desired size (for example thin wafers). The following examples illustrate these matrix formulations:

EXAMPLE 4

A hydrolyzed gelatin solution is prepared by dissolving 30 g of gelatin in 1 L of water and heating at 121° C. at 1.03 bar for one hour. The solution is allowed to cool to room temperature. One gram of S,R-formoterol or an S,R-formoterol salt is dissolved in the solution. A mold in the form of an aluminum film containing 75 cylindrical depressions (each depression being about 0.5 cm diameter and 1 cm deep) is cooled to about −192° C. in liquid nitrogen contained in a stainless steel tray. One half milliliter of the mixture is introduced into each depression and frozen. The mold is placed in a vacuum chamber at room temperature and a vacuum of 0.3 mm Hg is applied for 12 hours. The freeze dried matrices, each containing 0.5 mg of formoterol (about 10 to 20 unit doses), are covered with a pealable aluminum seal.

EXAMPLE 5

Twenty grams of acacia is placed in a dry 1 L flask and about 10 mL of absolute alcohol is added. The flask is shaken to wet the acacia powder, and 500 mL of distilled water is introduced and shaken to yield a homogeneous solution. Thirty grams of polyvinylpyrrolidine and 1 g of S,R-fornoterol are dispersed into the solution with the aid of ultrasonic vibration. The final volume is adjusted to 1L with distilled water and 1 mL of the composition is added to each container (for multiple doses) or 20 to 50 µL is added to each container (for a unit dose). The lyophilization is carried out as described above. The container is then sealed with a pealable seal.

The matrices prepared according to example 4 may be provided to the user as a component of a kit. The other component of the kit is a container containing the appropriate amount of buffered saline, or other suitable aqueous vehicle, sufficient to dissolve a single matrix (wafer) and provide a sterile, homogenous solution of precisely controlled concentration. Thus, for example, a wafer may contain 2–5 mg of S,R-formoterol, which is the range for one unit dose for inhalation. In that case, the second container may contain 5 mL of saline. The second container containing the saline may be a sealed nebulizer reservoir. In use, the wafer would be transferred from its sealed blister pack into a nebulizer reservoir and combined with the saline components. The wafer dissolves within seconds and provides the solution for a single inhalation session.

Alternatively, matrices may be prepared in accordance with example 5, wherein the container in which the solution is lyophilized is a reservoir for use in a nebulizer. The kit would then comprise the matrix in a sealed nebulizer reservoir as the first component and a container containing the appropriate amount of buffered saline, or other suitable aqueous vehicle, sufficient to dissolve the matrix as the other container.

A study was carried out to determine the stability of a formulation comprised of S,R-formoterol and lactose, in the presence and absence of 5% water. A series of amber 20 mL, crimp-topped vials were prepared to contain S,R-formoterol and lactose. The contents of the vials were (1) dry S,R-formoterol; (2) 20% dry S,R-formoterol and 80% lactose; and (3) 19% S,R-formoterol, 76% lactose and 5% $H_2O$. The vials were placed in a 60° C. or a 40° C. oven and then assayed via high-performance liquid chromatography (HPLC) at 256 nanometers. The only significant degradation seen was in the vial containing 5% $H_2O$. This sample represents the worst case scenario for a drug/excipient interaction as stated in *Drug Stability* (Carstensen et al., pp.379–380). These data indicate that under accelerated conditions for excipient interaction studies, the combination of α-lactose monohydrate and water adversely affects the stability of S,R-formoterol, while a solid dose S,R-formoterol/lactose composition in the absence of 5% moisture does not show this high degree of degradation. These results are presented in Table 1, below.

TABLE 1

| Sample | Potency (%); 60°/75% RH | | Potency (%); 40° C./75% RH | |
|---|---|---|---|---|
| | 1 week | 1 month | 1 month | 3 months |
| (S,R) formoterol (Fm) | 99.1 | 98.9 | 99.8 | 98.5 |
| (S,R) Fm/lactose | 101.0 | 99.0 | 99.4 | 98.8 |
| (S,R) Fm/water | 99.1 | 98.9 | 98.4 | 98.3 |
| (S,R) Fm/lactose/water | 94.7 | 3.2 | 98.9 | 95.7 |

The following tests were used to characterize the pharmacology of (S,R)-formoterol and (S,R)-desformoterol.

First Series (R,RlS,S)-, (R,R)-, (S,R)-, (R,S)-, and (S,S)-formoterol were evaluated for their affinities to $β_1$ and $β_2$-receptors, their capacity to stimulate cAMP production (intrinsic activity), and their propensity to cause densensitization.

Formoterol and its enantiomers were evaluated in radiolabeled binding assays with [$^{125}$I]-iodopindolol (45–85 pM) to determine their respective affinities for recombinant human $β_1$- and $β_2$-adrenergic receptors expressed in *Spodoptera frugiperda* (Sf9) cells. Each compound was tested at various concentrations ($10^{-9}$–$10^{-3}$ M) in each of the two receptor membrane preparations. Dissociation constants ($K_{ds}$) were then determined and tabulated in Table 2.

TABLE 2

| Formoterol | $K_d$ (nM) | | $β_2$ Selectivity ($β_1/β_2$) | Intrinsic Activity (cAMP) |
|---|---|---|---|---|
| | $β_1$ | $β_2$ | | |
| (R,R/S,S) | 192 | 5.2 | 36.9 | 0.94 |
| (R,R) | 113 | 2.9 | 39.0 | 1.02 |
| (S,R) | 2,500 | 75 | 33.0 | 0.91 |
| (R,S) | 133 | 103 | 1.3 | 0.65 |
| (S,S) | 6,800 | 3,100 | 2.2 | 0.18 |
| Isoproterenol | 24 | 37 | 0.6 | 1.00 |

(R,R)-Formoterol had the greatest potency and the most selectivity (nearly 40-fold) at the $β_2$-adrenergic receptor.

The assessment of intrinsic activity was evaluated in BEAS-2B cells grown to confluence. Cells were washed and stimulated for 0–30 minutes with PBS containing ascorbate, a phosphodiesterase inhibitor, and either vehicle or 100-times the $K_d$ concentration of formoterol or its isomers. Samples were assayed for cAMP by radioirmmunoassay. (R,R/S,S)-, (R,R)-, and (S,R)-formoterol displayed high intrinsic activities relative to isoproterenol (intrinsic activity set to 1.0). Whereas (R,S)- and (S,S)-formoterol showed moderate and low intrinsic activities, respectively.

Beta$_2$-receptor responsiveness was evaluated in BEAS-2B cells pretreated for 0–48 hours with formoterol or its isomers. The pretreated cells were then stimulated with 10 µM isoproterenol and cAMP accumulation was measured. Pretreatment with each of the compounds at $K_d$ concentrations produced a rapid loss of isoproterenol-stimulated cAMP production ($t_{1/2}$<1 hour for each compound). The (R,S)- and (S,S)-enantiomers had significant but smaller effects. Qualitatively similar, but slightly more rapid effects were observed with pretreatment with concentrations 100-times the $K_d$.

Beta$_2$-adrenergic receptor down-regulation was evaluated in BEAS-2B cells treated for 0–38 hours with formoterol and its isomers at either the $K_d$ or 100-times the $K_d$ concentration. Receptor density was estimated by one-point analysis using [$^{125}$I]iodopindolol. (R,R/S,S)-, (R,R)-, and (S,R)-formoterol at the $K_d$ elicited a rapid down-regulation ($t_{1/2}$~4 hours). (S,S)-Formoterol, on the other hand, displayed a time-course significantly slower ($t_{1/2}$~6 hours) than those of the other compounds. Down-regulation at higher concentrations (100-times the $K_d$) occurred at a slightly faster rate, and the relatively greater effects of (R,R/S,S)-(R,R)-, and (S,R)-formoterol on receptor loss still prevailed over those observed for the (R,S)- and (S,S)-enantiomers.

Second Series (R,S)- and (S,S)-desformoterol were screened, in duplicate at three concentrations ($10^{-9}$, $10^{-7}$, $10^{-5}$ M), for binding to human $β_1$ and $β_2$-adrenergic receptors. Compounds that inhibited specific binding ≧50% were then tested further at ten concentrations in duplicate in order to obtain full competition curves. Reference compounds were simultaneously tested at eight concentrations. $IC_{50}$ values (concentration required to inhibit 50% of specific binding) were determined by nonlinear regression analysis and tabulated in Table 3.

TABLE 3

| Compound | $IC_{50}$ (nM) | |
| --- | --- | --- |
|  | $\beta_1$ | $\beta_2$ |
| (R,S)-Desformoterol | 1,790 | 3,140 |
| (S,R)-Desformoterol | — | 1,830 |
| Atenolol | 1,430 | — |
| ICI 118551 | — | 2.4 |

The binding of (R,S)-desformoterol was comparable to that of atenolol at the $\beta_1$-site, and an $IC_{50}$ was not determined for (S,R)-desformoterol because only 22% inhibition was attained at $10^{-5}$ M.

The comparative results are shown in Table 4:

TABLE 4

| | $\beta_1$ | $\beta_2$ | $\beta_2$ Selectivity ($\beta_1/\beta_2$) | Intrinsic Activity (cAMP) |
| --- | --- | --- | --- | --- |
| (R)-Albuterol (mM) | | | | |
| Second series | 9.9 | 4.1 | 2.4 | |
| First series | 1.540 | 0.236 | 6.5 | 0.44 |
| Desformoterol (nM) | | | | |
| Second series (human) | | | | |
| (R,R/S,S) | 5,142 | 81.3 | 63 | |
| (R,R) | 3,180 | 35.6 | 89 | |
| (S,S) | 64,710 | >10,000 | — | |
| (R,S) | 1,790 | 3,140 | 0.6 | |
| (S,R) | — | 1,830 | — | |
| Formoterol (nM) | | | | |
| Second series | | | | |
| (R,R/S,S) | 1,500 | 900 | 1.6 | |
| (R,R) | 710 | 150 | 4.7 | |
| (S,S) | 7,100 | 2,200 | 3.2 | |
| (human) | | | | |
| (R,R/S,S) | 344 | 4.9 | 70 | |
| (R,R) | 199 | 2.3 | 86 | |
| Formoterol (nM) | | | | |
| First series | | | | |
| (R,R/S,S) | 192 | 5.2 | 37 | 0.94 |
| (R,R) | 113 | 2.9 | 39 | 1.02 |
| (S,S) | 6,800 | 3,100 | 2.2 | 0.18 |
| (R,S) | 133 | 103 | 1.3 | 0.65 |
| (S,R) | 2,500 | 75 | 33 | 0.91 |

What is claimed is:

1. A method for inducing bronchodilation, relieving or preventing bronchospasm, reversing or preventing bronchoconstriction and treating reversible obstructive pulmonary disorders which comprises administering to a human in need of bronchodilation a therapeutically effective amount of (S,R)-formoterol, or a pharmaceutically acceptable salt thereof, said (S,R)-formoterol containing less than 10% by weight of other isomers of formoterol.

2. A method according to claim 1 wherein bronchodilation is induced by administering an amount of (S,R)-formoterol sufficient to effect bronchodilation but insufficient to cause side effects.

3. The method of claim 1 wherein (S,R) formoterol is administered by inhalation or oral administration.

4. The method according to claim 3 wherein the amount administered by inhalation is about 100 μg to about 10 mg per day.

5. A method according to claim 3 wherein said amount is administered in divided doses from two to four times a day.

6. A pharmaceutical composition in the form of a tablet, capsule or aerosol formulation which comprises a pharmaceutically acceptable carrier suitable for a tablet, capsule or aerosol and an amount of (S,R)-formoterol, or a pharmaceutically acceptable salt thereof, sufficient to alleviate bronchospasms, said (S,R)-formoterol containing less than 10% by weight of other isomers of formoterol.

7. A pharmaceutical composition according to claim 6 adapted for administration by inhalation wherein the amount of (S,R) formoterol per unit dose is about 600 μg to about 2.5 mg.

8. A pharmaceutical composition according to claim 6 in the form of an aerosol formulation, wherein said pharmaceutically acceptable carrier comprises a propellant.

9. A pharmaceutical composition according to claim 6, wherein said pharmaceutically acceptable carrier comprises an open matrix of a polysaccharide or hydrolyzed gelatin.

10. A pharmaceutical composition according to claim 6 for oral administration.

11. A pharmaceutical composition according to claim 10 in the form of a syrup.

12. A pharmaceutical composition according to claim 10 in the form of a tablet or a capsule.

13. An anhydrous pharmaceutical composition according to claim 10.

14. A pharmaceutical composition according to claim 12 in sustained release form.

15. A pharmaceutical composition for aerosol administration which comprises a pharmaceutically acceptable carrier suitable for an aerosol formulation and an amount of (S,R)-formoterol, or a pharmaceutically acceptable salt thereof, sufficient to provide from 100 μg to 100 mg of (S,R)-formoterol per unit dose, said (S,R)-formoterol containing less than 10% by weight of other isomers of formoterol.

16. A pharmaceutical composition according to claim 15, wherein said pharmaceutically acceptable carrier comprises a propellant.

17. A pharmaceutical composition according to claim 15, wherein said pharmaceutically acceptable carrier comprises an open matrix of a polysaccharide or hydrolyzed gelatin.

* * * * *